United States Patent
Liu

[11] Patent Number: 5,969,165
[45] Date of Patent: Oct. 19, 1999

[54] ISOLATION AND PURIFICATION OF PACLITAXEL AND OTHER RELATED TAXANES BY INDUSTRIAL PREPARATIVE LOW PRESSURE CHROMATOGRAPHY ON A POLYMERIC RESIN COLUMN

[75] Inventor: Jian Liu, Fredericton, Canada

[73] Assignee: 508037 (NB) Inc., Fredericton, Canada

[21] Appl. No.: 09/226,192

[22] Filed: Jan. 7, 1999

[51] Int. Cl.$^6$ .................................................. C07D 305/14
[52] U.S. Cl. ............................................ 549/510; 549/511
[58] Field of Search ...................................... 549/510, 511

[56] References Cited

U.S. PATENT DOCUMENTS

| | | | |
|---|---|---|---|
| 5,620,875 | 4/1997 | Hoffman et al. | 435/123 |
| 5,670,673 | 9/1997 | Rao | 549/510 |

*Primary Examiner*—Ba K. Trinh
*Attorney, Agent, or Firm*—Paul S. Sharpe; Marks & Clerk

[57] ABSTRACT

A high yield and high purity method for obtaining taxane analogues from a source containing taxanes. The method employs a polymeric resin membrane for separating the analogues under low pressure without the use of complex and expensive separation/purification steps currently provided in the art.

20 Claims, No Drawings

ISOLATION AND PURIFICATION OF PACLITAXEL AND OTHER RELATED TAXANES BY INDUSTRIAL PREPARATIVE LOW PRESSURE CHROMATOGRAPHY ON A POLYMERIC RESIN COLUMN

FIELD OF THE INVENTION

The present invention relates to a separation technique and more particularly, the present invention relates to techniques to separate paclitaxel and related taxanes.

BACKGROUND OF THE INVENTION

Paclitaxel is a well known chemotherapeutic drug for treatment of various metastatic cancers. It has been approved by FDA and HPB for the treatment of ovarian and breast cancers.

The compound is a natural product, primarily extracted from the bark of the Pacific yew tree, *Taxus brevifolia,* and is also found in *T. baccata, T. walichiana, T. yunnanensis* and *T. canadensis.*

The concentration of paclitaxel in various raw materials is typically low, for example, on the order of between 0.0004 and 0.01% (w/w) in the bark of Pacific yew. Such low concentration render the extraction and purification of the compound to pharmaceutical grade from raw materials very challenging, and heretofore impractical on a commercial scale. Various normal phase chromatography and reverse phase chromatography as well as low and high pressure column chromatography techniques have been developed to purify paclitaxel from a crude extract of raw material.

The success of low pressure chromatography greatly depends on the nature of the column. Various problems are associated with the use of silica gel and alumina trioxide, all of which are classical supports of the stationary phase in partition systems. They form a stable stationary phase with most solvent systems, but it is a strong absorbent and may participate in the separation process to the extent that chromatographic behaviour and recovery of samples are affected.

Chromatographic methods have been developed to detect and isolate paclitaxel from various Taxus species on analytical and preparative basis. These isolation processes are mainly conducted on a small laboratory scale and suffer from low selectivity, recovery and high production cost, thereby presenting a serious and unfulfilled need for an economically practicable method for separating the valuable anti-tumor compound paclitaxel from its close analog cephalomanine as well as other closely related taxanes.

Prior art methods disclose the use of various types of chromatographic techniques to separate paclitaxel and related taxanes, including normal phase and reverse phase chromatography on a silica gel or bonded silica gel column. The prior art methods are end up at low yield, high production cost or involved multiple separation steps which were difficult to scale up to large industrial scale production.

Characteristic of the prior art is U.S. Pat. No. 5,620,875, issued Apr. 15, 1997, to Hoffman et al. The document teaches the separation of paclitaxel and other taxanes by multiple step hexane extractions and high performance liquid chromatography (HPLC). The process is involved, labor intensive and only provides moderate yields of the desired compounds.

In U.S. Pat. No. 5,670,673, issued Sep. 23, 1997, to Rao, the isolation and purification of Taxol and its analogues is delineated. The process includes the use of reverse phase liquid chromatography on a C18 adsorbent with elution of the adsorbed analogues. Although a meritorious procedure, limitations exist with this technique in terms of productivity and purity of compounds obtained.

The present invention provides a simple separation method based on a polymeric resin column which is devoid the limitations of the existing methodology.

SUMMARY OF THE INVENTION

It is therefore an object of this invention to provide a simple and more cost effective method for economical isolation and purification of the important taxanes, such as 13-acetyl-9-dihydrobaccatin III, 10-deacetylbaccatin III, baccatin III, cephalomanine and paclitaxel.

Conventional methods for the isolation of taxanes, including paclitaxel, 13-acetyl-9-dihydrobaccatin III and baccatin III generally comprise the steps of extracting taxanes from raw materials with an alcoholic solvent, defatting the extract, and separating and purifying the individual taxane by chromatography.

One object of the present invention is to provide a method of isolating and purifying taxane analogues from a source containing taxanes, comprising:

extracting a source of taxanes in an organic extractant;

coating a work absorbent medium with the extractant and loading the medium in a column, the column containing an absorbent agent;

eluting, in a first step, with an organic solvent mixture at a pressure of between 10 and 20 psi to generate fractions containing taxane compounds;

crystallizing the fractions to provide a solid taxane compound and a mother liquor; concentrating the mother liquor; and eluting, in a second step, with a polar solvent mixture the mother liquor through a polymeric resin to provide at least a second taxane compound.

A further object of the present invention is to provide a method of isolating and purifying taxanes from a source containing taxanes, comprising:

providing a source of taxanes;

extracting the taxanes from the source into an organic extraction medium to provide an organic layer containing taxane compounds;

treating a support material with the organic layer;

providing a low pressure column containing an absorbent agent;

eluting, in a first step, an organic solvent through the column to elute purified taxane fractions;

crystallizing the taxane fractions to provide a first taxane analogue and a mother liquor;

eluting, in a second step, the mother liquor through a polymeric resin in a chromatographic column to purify and elute at least a second taxane analogue and a third taxane analogue; and collecting separated taxane analogues.

A still further object of the present invention is to provide a method of isolating and purifying taxanes from a source containing taxanes, comprising:

providing a source of taxanes;

extracting the taxanes from the source into an organic extraction medium to provide an organic layer containing taxane compounds;

treating a support material with the organic layer;

providing a low pressure column containing an absorbent agent;

eluting, in a first step, at a pressure of between 10 and 20 psi, an organic solvent through the column to elute purified taxane fractions and remove flavonoid and lignan impurities;

crystallizing the taxane fractions to provide a first taxane analogue and a mother liquor;

eluting, in a second step, at a pressure of 30 psi, the mother liquor through a polystyrene DVB resin in a chromatographic column to purify and elute at least a second taxane analogue and a third taxane analogue;

eluting, in a third step, the second taxane analogue and the third taxane analogue through a normal phase silica gel column to purify the second taxane analogue and the third taxane analogue; and collecting separated taxane analogues.

DETAILED DESCRIPTION OF THE PREFERRED EMBODIMENTS

The initial source of taxanes was the plant material, *Taxus canadensis,* which is abundant in Eastern Canada. The twigs and needles or mixture thereof from *Taxus canadensis* were used. The material may be fresh or dried.

The raw material was ground and extracted with methanol at 60° C. for five hours and filtered. The methanol extract was mixed with charcoal and left to stand at room temperature for one hour. This was then filtered. The filtrate was concentrated to about 15% of original volume by evaporation. A 1:1 water:dichloromethane mixture (v/v) was added to the concentrate to obtain a paclitaxel enriched portion (organic layer).

The organic layer was concentrated to a reduced volume and coated on a support material, in this case, the supporting material is Celite 545.

The coated material was loaded on to the top of an industrial preparative column, for example, a 150 mm×1500 mm column and packed with the absorbent agent $Al_2O_3$. The column was eluted with a mixture of hexane:acetone (start 100:0 end at 45:55) under a pressure of between 10 psi and 20 psi. The fractions containing taxanes were collected and analyzed by thin layer chromatography (TLC) and subsequently combined according TLC results.

The fractions collected were then concentrated under vacuum, the resulting material was dissolved in methanol and kept at room temperature overnight. The crystal formed was filtered out and washed with methanol, then recrystallized from acetone. 13-Acetyl-9-dihydrobaccatin III was obtained as white crystal.

The mother liquor was concentrated to dryness and the residue was dissolved in acetone. The acetone solution was mixed with a polymeric resin (Dowex™ resin, polystyrene-DVB). The mixture was evaporated under vacuum to remove acetone. The resulting powder was subjected to low pressure chromatography. The industrial scale (150 mm×1500 mm) chromatographic column was packed with Dowex™ resin and eluted with acetone:water (45:55, v/v) at a flow rate 150 ml/min under a operating pressure of 30 psi. Fractions of approximately 2L/each were collected and these were monitored by TLC and HPLC. The fractions which contained baccatin III and 10-deacetylbaccatin III were combined and evaporated under vacuum to remove substantially all of the organic solvent, then diluted with water and extracted with $CH_2Cl_2$. The extract was then concentrated to dryness and the resulting residue was then dissolved in $EtOA_c$ and purified by normal phase silica gel column with hexane:$EtOA_c$ as the solvent system (start 5:5 end at 35:65). The baccatin III and 10-deacetylbaccatin-III was finally obtained as white powder with a purity of greater than 98%.

The fractions which contained paclitaxel and cephalomanine were combined and evaporated under vacuum to remove substantially all of the acetone, then partitioned between water and $CH_2Cl_2$. The organic layer was separated and evaporated to dryness under vacuum. The residue was dissolved in methanol. To the methanol solution approximately 30% (w/v) of water was added and the mixture was warmed to 60° C. for five minutes, then kept in room temperature overnight. The crude crystalline solid from the methanol solution was filtered out and dried under vacuum between 70° C. and 75° C. The solid was analyzed by HPLC. It consisted approximately 70% of paclitaxel and 25% of cephalomanine, and some other taxanes.

The crude paclitaxel can be processed according to one of three alternative procedures. In a first possibility, it was dissolved in acetone and purified by reverse phase column chromatography. The column was packed with polymeric resin (Diaion resin, HP2MG) and eluted with acetonitrile:water (45,55). Paclitaxel was obtained as white crystal with a purity of greater than 99%. Cephalomanine was obtained as a white powder in a purity of greater than 98%.

Alternatively, as a second processing approach, the purification of paclitaxel and cephalomanine was carried out through a chemical reaction process and then purified by bonded silica gel reverse phase column chromatography. The crude paclitaxel, cephalomanine mixture was dissolved in $CH_2Cl_2$ or $CHCl_3$ (1:10, w/v), and reacted with 10 equivalent of bromine in a round bottom flask that placed in an ice bath (between 0° C. and 5° C.) for approximately 40 minutes. The resulting mixture of paclitaxel and 2",3"-bromocephalomanine were readily separated by a reverse phase chromatographic column ($C_{18}$ or phenyl), eluting solvent $CH_3CN:H_2O$ (45:55). Paclitaxel was obtained as white crystal in a purity of greater than 99%. 2",3"-bromocephalomanine was obtained as a mixture of diastereomers, which were reacted with activated zinc in acetic acid at room temperature, and then purified by flash column chromatography to obtain pure cephalomanine having a purity of greater than 95%.

In a third alternative, the paclitaxel and bromocephalomanine were purified through normal phase silica gel column. The eluting solvent systems may comprise hexane:$EtOA_c$ (start 6:4 end at 4:6), or $CH_2Cl_2:Me_2CO$ (start 8:2 end at 65:35) or $CHCl_2:EtOA_c$ (start 75:25, end 6:4). From this method, paclitaxel was obtained as white crystal with a purity exceeding 99%, with cephalomanine present in an amount of less than 0.2%.

Having discussed the invention, more precise reference will now be made to the invention by way of the examples.

EXAMPLE 1

Approximately 200 kilograms of dried needles and twigs of *Taxus canadensis* were extracted with 1,000 liters of methanol at 60° C. in an industrial multi-functional extractor for five hours and then filtered. The raw materials were extracted with 700 liters of methanol at a temperature of between 55° C. and 60° C. for another four hours and filtered. The filtrate was combined and mixed with 10 kilograms of activated carbon (5% w/w) and kept at room temperature for one hour, then filtered to remove the activated carbon. The filtrate was then concentrated to approximately 100 liters under vacuum, then 300 liters of water:dichloromethane (1:1) was added. The organic layer was collected and the aqueous solution was extracted two more times with 200 liters of dichloromethane. The dichloromethane solution was combined and evaporated under vacuum to become a slurry form, then diluted with 20 liters of acetone.

The acetone solution was coated on to 20 kilograms of Celite 545. The coated material was air dried and was then loaded on to the top of three low pressure industrial chromatographic columns (dimension: 150×15 cm). Each column was packed with 15 kilograms of alumina oxide ($Al_2O_3$) absorbent. It will be appreciated that the exact dimension of the columns is not crucial as long as the columns are sufficiently large to hold the amount of $Al_2O_3$ required for the separation. Use of alumina oxide is effective to absorb flavonoids and lignans which are co-extracted from the source material. These are also difficult to remove and become a problem for the final purity of the product paclitaxel.

The columns were eluted with the solvent system hexane:acetone (start 100:0 end at 45:55) under a pressure between 10 and 15 psi with a flow rate at approximately 150 ml/min.

The fractions containing taxanes were collected and combined according to thin layer chromatography (TLC) results, and were then concentrated under vacuum to remove all solvents. The resulting material was dissolved in methanol and kept at room temperature overnight to yield needle-like crystals. The crystals were filtered and recrystallized from acetone to further yield white needle-like crystals identified as 13-acetyl-9dihydrobaccatin III, having a purity of greater than 96% yield (148 grams) (0.074% based on the raw material).

The mother liquid from the 13-acetyl-9dihydrobaccatin III crystallization was concentrated to dryness under vacuum. The residue was dissolved in three liters of acetone. The acetone solution was mixed with 1.5 kilograms of a polystyrene-divinylbenzene, copolymer resin. The mixture was evaporated to remove the solvent and the resulting powder was loaded on the top of a low pressure industrial chromatographic column packed with polystyrene-divinylbenzene copolymer resin, and eluted with 45% acetone in water at a flow rate of 150 ml/min. under an operating pressure below than 30 psi. Fractions of 2 L/each were collected and these were monitored by TLC and HPLC.

The fractions which contained paclitaxel and cephalomanine were combined and evaporated under vacuum to remove most of the acetone, then diluted with deionized water and extracted three times with 2.5 liter of dichloromethane. The organic layer was concentrated to dryness under vacuum, the residue was dissolved in one liter of methanol.

To the methanol solution, approximately 30% (v/v) of water was added and the mixture was warmed to 60° C. for a few minutes then kept at room temperature overnight. The crude crystalline solid from the methanol solution was filtered out and dried in a vacuum oven at a temperature of between 70° C. and 75° C. The solid consisted of approximately 70% paclitaxel and 25% cephalomanine in a yield of 31 grams.

The crude paclitaxel (30 g) was dissolved in 200 ml of acetonitrile and diluted with 250 ml of deionized water and pumped into the top of a low pressure chromatography column (size: 10×150 cm) and packed with a polymer resin (Diaion, macroporous polymethacrylate resin). After the sample was pumped, the column was eluted with a step gradient of 35, 40, 45 and 50% acetonitrile in water. The change of solvent was indicated by the results of the TLC and HPLC of the fractions.

Fractions of approximately 1 L/each were collected and monitored by TLC and HPLC analysis. The flow rate was 75 ml/min. The column fractions which contained paclitaxel or cephalomanine were combined individually. The two combined solutions were allowed to stand at a temperature of approximately 5° C. until crystallization of the individual compound was completed.

The crystals were filtered separately and both were recrystallized from 65° C. methanol in water.

Paclitaxel was obtained as white needle-like crystals with a purity of greater than 99% and a yield of 18.5 g (0.009%).

Cephalomanine was obtained as white needles with a purity of greater than 98% and a yield of 6.5 g (0.003%).

The fractions contained baccatin III and 10-deacetylbaccatin III from the previous step were combined and evaporated under vacuum to remove substantially acetone, then partitioned between three liters of water and dichloromethane (1:1 v/v). The organic layer was concentrated to dryness and the residue was subjected for normal phase chromatography. The dimension of the column used was 4"×4', packed with silica gel (200–300 mesh). The eluting solvent was a step gradient of hexane:ethyl acetate (start 50:50 end at 35:65). Fractions of approximately 1,000 ml/each were collected and each was monitored by TLC.

The fractions contained baccatin III or 10-deacetylbaccatin III were separately collected and combined according TLC results, then concentrated to dryness.

The baccatin III part was dissolved in 200 ml of methanol and kept in a refrigerator overnight. The white crystals formed were filtered out and recrystallized from methanol to yield baccatin III as white crystals in a yield of 7.5 g (0.003%).

The crude 10-deacetylbaccatin III was dissolved in 150 ml acetone and then diluted with 150 ml of hexane. The mixture was kept at room temperature overnight. The white crystals formed were filtered and recrystallized from same solvent to yield 10-deacetylbaccatin III as white crystals. The yield was 15 g (0.007%).

EXAMPLE 2

Using similar apparatus and methodology as used in Example 1, crude paclitaxel was obtained. The crude paclitaxel was dissolved in 300 ml of dichloromethane which was added to a 1,000 ml three neck round bottom flask. The flask was replaced in an ice-bath and the solution stirred with a magnetic stirrer. When the temperature reached approximately 5° C., a solution of bromine (10 equivalents) in dichloromethane (1:1 v/v) was added slowly with stirring. The cephalomanine to bromine ratio was 1 to 10 moles.

The brominating was monitored by TLC analysis between five and 10 minutes. The reaction mixture was then diluted with 300 ml of dichloromethane and transferred to a separatory funnel after the reaction was completed (completion time required between 40 and 50 minutes). To the reaction mixture, 350 ml of 10% aqueous sodium thiosulfate ($Na_2S_2O_3$) was added to absorb any excess bromine. The dichloromethane layer was separated and washed with water and brine, and then concentrated to dryness under vacuum. A light brown powder was obtained.

EXAMPLE 3

The crude material (10 g) from Example 2 was dissolved in 120 ml of acetonitrile which was diluted with 150 ml of deionized water. The solution was pumped into the top of a reverse phase chromatography column (5×100 cm) packed with C$_{18}$ bonded silica gel.

The column was eluted with acetonitrile:water (45:55) under an operating pressure of between 30 and 40 psi. The flow rate was 30 ml/min. The fractions were collected (250 ml/each), monitored by TLC and combined.

The portion containing paclitaxel was refrigerated overnight; the crystals formed were filtered and recrystallized from 70% methanol. Paclitaxel was obtained as white needle-like crystals having a purity of greater than 99% in a yield of 6:1 g.

The fractions containing 2",3"-bromocephalomanine were combined, which partitioned between water and dichloromethane. The organic layer was collected and evaporated to dryness under vacuum. The residue was dissolved in 150 ml of methanol, which was diluted with 50 ml of water to obtain needle-like crystals. The off-white crystal was recrystallized from methanol:water to yield 2",3"-bromocephalomanine as white crystals.

Two grams of 2",3"-bromocephalomanine were dissolved in 30 ml of AcOH and freshly activated zinc (2 g) was added. The mixture was stirred for three hours at room temperature and the reaction was monitored by TLC. After TLC analysis showed the reaction was completed, the mixture was partitioned between dichloromethane and 10% NaHCO$_3$ (300 ml, 2:1). The organic layer was washed with water and concentrated to dryness. The crude product was purified by flash chromatography to give cephalomanine as white powder.

EXAMPLE 4

The crude material (10 g) from Example 2 was dissolved in 120 ml of dichloromethane. The organic layer was concentrated to dryness and the residue was subjected for normal phase chromatography. The dimension of the column used was 4"×4' packed with silica gel (between 200 and 300 mesh). The eluting solvent was a step gradient of dichloromethane:ethyl acetate (start 75:25 end at 6:4), for the separation of paclitaxel and 2",3"-bromocephalomanine the solvents system of hexane:ethyl acetate (start 6:4 end at 4:6) and dichloromethane:acetone (start 8:2 end at 65:35) also can be used. Fractions of approximately 500 ml/each were collected, and each was monitored by TLC.

The fractions contained paclitaxel and 2",3"-bromocephalomanine were separately collected and combined according TLC results, then concentrated to dryness.

The paclitaxel part was dissolved in 100 ml of methanol and diluted with 35 ml of water, then kept refrigerated. The white crystals formed were filtered and recrystallized from methanol:water to yield paclitaxel (5.5 g) as white crystals.

The crude 2",3"-bromocephalomanine was dissolved in 50 ml acetone and then diluted with 50 ml of hexane. The mixture was kept at room temperature overnight. The white crystals formed were filtered and recrystallized from same solvent to yield 2",3"-bromocephalomanine as white crystals.

The following examples illustrate the compounds in structural form.

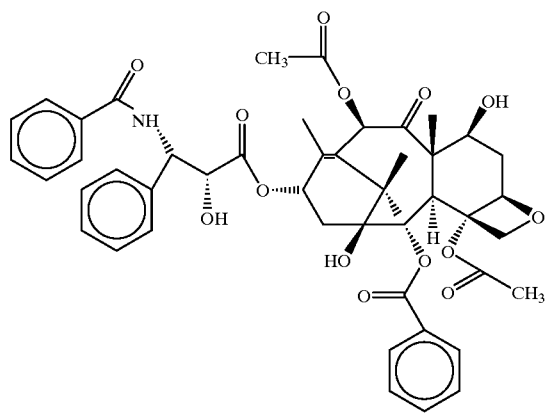

Paclitaxel

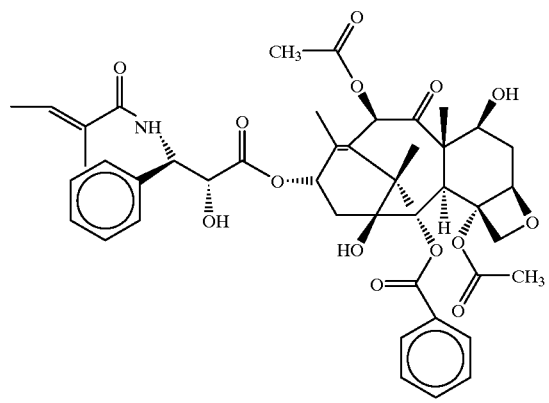

Cephalomanine

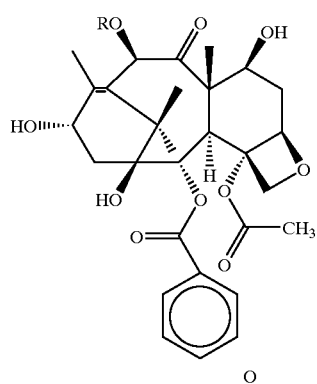

Baccatin III = R = (acetyl)
10-deacetylbaccatin IV = R = H

-continued

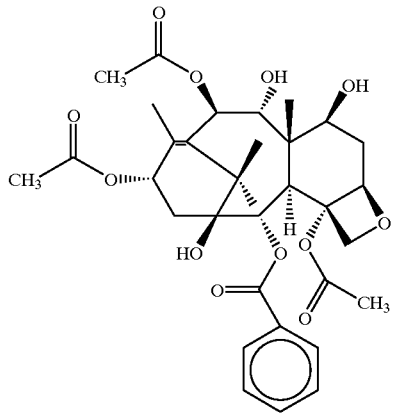

13-acetyl-9-dihydrobaccatin III

Although embodiments of the invention have been described above, it is not limited thereto and it will be apparent to those skilled in the art that numerous modifications form part of the present invention insofar as they do not depart from the spirit, nature and scope of the claimed and described invention.

I claim:

1. A method of isolating and purifying taxane analogues from a source containing taxanes, comprising:
    extracting a source of taxanes in an organic extractant;
    coating a work absorbent medium with said extractant and loading said medium in a column, said column containing an absorbent agent;
    eluting, in a first step, with an organic solvent mixture at a pressure of between 10 and 20 psi to generate fractions containing taxane compounds;
    crystallizing said fractions to provide a solid taxane compound and a mother liquor; concentrating said mother liquor; and
    eluting, in a second step, with a polar solvent mixture said mother liquor through a polymeric resin to provide at least a second taxane compound.

2. The method as set forth in claim 1, further including the step of removing lignan and flavonoid impurities in said first step.

3. The method as set forth in claim 1, wherein said source of said taxanes comprises a plant source.

4. The method as set forth in claim 3, wherein said plant source is selected from a member of the group comprising *Taxus brevifolia, Taxus baccata, Taxus walichiana, Taxus yunnanensis,* and *Taxus canadensis.*

5. The method as set forth in claim 3, wherein said taxanes include at least 13-acetyl-9-dihydrobaccatin III, 10-deacetylbaccatin III, baccatin III, cephalomanine, paclitaxel.

6. The method as set forth in claim 1, wherein said organic extractant comprises dichloromethane.

7. The method as set forth in claim 1, wherein said weak absorbent medium comprises Celite 545.

8. The method as set forth in claim 1, wherein said absorbent agent comprises aluminum oxide.

9. The method as set forth in claim 1, wherein said first step organic solvent mixture comprises hexane and acetone.

10. A method of isolating and purifying taxanes from a source containing taxanes, comprising:
    providing a source of said taxanes;
    extracting said taxanes from said source into an organic extraction medium to provide an organic layer containing taxane compounds;
    treating a support material with said organic layer;
    providing a low pressure column containing an absorbent agent;
    eluting, in a first step, an organic solvent through said column to elute purified taxane fractions;
    crystallizing said taxane fractions to provide a first taxane analogue and a mother liquor;
    eluting, in a second step, said mother liquor through a polymeric resin in a chromatographic column to purify and elute at least a second taxane analogue and a third taxane analogue; and
    collecting separated taxane analogues.

11. The method as set forth in claim 10, further including the step of removing lignan and flavonoid impurities in said first step.

12. The method as set forth in claim 10, further including the step of grinding said source of taxanes and extracting with methanol.

13. The method as set forth in claim 12, further including the step of mixing extract with charcoal, filtering and evaporating to form a concentrate.

14. The method as set forth in claim 13, wherein said support material comprises Celite 545.

15. The method as set forth in claim 1, wherein said organic solvent comprises a mixture of acetone and hexane.

16. The method as set forth in claim 15, wherein said organic solvent is passed through said column at a pressure of between 10 and 20 psi.

17. The method as set forth in claim 1, further including the step of collecting and analyzing said taxane fractions by thin layer chromatography.

18. A method of isolating and purifying taxanes from a source containing taxanes, comprising:
    providing a source of said taxanes;
    extracting said taxanes from said source into an organic extraction medium to provide an organic layer containing taxane compounds;
    treating a support material with said organic layer;
    providing a low pressure column containing an absorbent agent;
    eluting, in a first step, at a pressure of between 10 and 20 psi, an organic solvent through said column to elute purified taxane fractions and remove flavonoid and lignan impurities;
    crystallizing said taxane fractions to provide a first taxane analogue and a mother liquor;
    eluting, in a second step, at a pressure of 30 psi, said mother liquor through a polystyrene DVB resin in a chromatographic column to purify and elute at least a second taxane analogue and a third taxane analogue;
    eluting, in a third step, said second taxane analogue and said third taxane analogue through a normal phase silica gel column to purify said second taxane analogue and said third taxane analogue; and
    collecting separated taxane analogues.

19. The method as set forth in claim 18, wherein said second taxane analogue comprises baccatin III and said third taxane analogue comprises 10-deacetylbaccatin III.

20. The method as set forth in claim 18, wherein said analogues have a purity of at least 98%.

* * * * *